(12) United States Patent
Hötten et al.

(10) Patent No.: US 6,531,450 B2
(45) Date of Patent: *Mar. 11, 2003

(54) USE OF MP52 OR MP121 FOR TREATING AND PREVENTING DISEASES OF THE NERVOUS SYSTEM

(75) Inventors: Gertrud Hötten, Herne (DE); Jens Pohl, Hambrücken (DE); Rolf Bechtold, Heidelberg (DE); Michael Paulista, Leimen (DE); Klaus Unsicker, Heidelberg (DE)

(73) Assignee: Biopharm Gesellschaft zur Biotechnologischen Entwicklung von Pharmaka, Heidelberg (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,490

(22) PCT Filed: Jul. 12, 1996

(86) PCT No.: PCT/EP96/03065

§ 371 (c)(1),
(2), (4) Date: May 18, 1998

(87) PCT Pub. No.: WO97/03188

PCT Pub. Date: Jan. 30, 1997

(65) Prior Publication Data

US 2002/0045568 A1 Apr. 18, 2002

(30) Foreign Application Priority Data

Dec. 7, 1995 (DE) .......................................... 195 25 416

(51) Int. Cl.$^7$ ...................... A61R 38/18; C07K 14/495; C07K 14/51
(52) U.S. Cl. ............................ 514/12; 514/23; 530/350
(58) Field of Search ....................... 514/12, 23; 530/350

(56) References Cited

U.S. PATENT DOCUMENTS 5,658,882 A * 8/1997 Celeste et al. ................ 514/12

FOREIGN PATENT DOCUMENTS

| WO | WO93/16099 | 8/1993 |
| WO | WO95/04819 | 2/1995 |
| WO | WO96/01316 | 1/1996 |

OTHER PUBLICATIONS

Patel SV. Pharmacotherapy of cognitive impairment in Alzheimer's disease: a review. J Geriatr Psychiatry Neurol. Apr. 1995; 8(2):81–95.*
Nathan et al. Cytokines in context. Journal of Cell Biology, (Jun., 1991) 113 (5) 981–986.*
Alberts et al. Molecular Biology of the Cell, Jan., 1994, Garland Publishing, Inc., New York, pp. 1142–1145.*
Flanders et al. Transforming growth factor–betas in neurodegenerative disease. Progress in Neurobiology, (Jan., 1998) 54 (1) 71–85.*
Sanchez–Capelo et al. Adenovirus–mediated over–expression of TGFbeta1 in the striatum decreases dopaminergic cell survival in embryonic nigral grafts. Neuroreport, (Jul. 13, 1999) 10 (10) 2169–73.*
Sauer et al. Glial Cell Line–Derived Neurotrophic Factor but not Transforming Growth Factor β3 Prevents Delayed Degeneration of Nigral Dopaminergic Neurons Following Striatal 6–Hydroxydopamine Lesion. Proceedings of the National Academy of Sciences, Sep. 1995, vol. 92, pp. 8935–8939.*
Marieb E N. In, Human Anatomy and Physiology, Second Edition. 1992. The Benjamin/Cummings Publishing Co., Inc. pp. 373–375.*
Kingsley D M. The TGF–beta superfamily: new members, new receptors, and new genetic tests of function in different organisms. Genes and Development, (Jan. 1994) 8 (2) 133–46. Apr. 1995.*

* cited by examiner

Primary Examiner—David S. Romeo
(74) Attorney, Agent, or Firm—Arent Fox Kintner Plotkin & Kahn

(57) ABSTRACT

The present invention concerns the use of biologically active MP52 or/and MP121 for the treatment and prevention of diseases of the nervous system or/and for the treatment of neuropathological situations which are caused by ageing of the nervous system. A pharmaceutical agent according to the invention for the treatment and prevention of diseases of the nervous system or/and for treating neuropathological situations which are caused by ageing of the nervous system therefore contains biologically active MP52 or/and MP121 as the active substance.

10 Claims, 7 Drawing Sheets

A

B

C

USE OF MP52 OR MP121 FOR TREATING AND PREVENTING DISEASES OF THE NERVOUS SYSTEM

The present invention concerns the use of MP52 or/and MP121, two growth or/and differentiation factors of the TGF-β superfamily, for the treatment and prevention of diseases of the nervous system or/and for the treatment of neuropathological situations which are caused by ageing of the nervous system. In addition the invention concerns pharmaceutical agents for the treatment or prevention of the above indications which contain MP52 or/and MP121.

Many growth factors from the TGF-β superfamily (Kingsley, Genes & Development 8, 133–146 (1994) and the literature cited therein) are relevant for a wide range of medical treatment methods and applications which in particular concern wound healing and tissue regeneration. These include in particular members of the TGF-β (Transforming Growth Factor, see e.g. Roberts and Sporn, Handbook of Experimental Pharmacology 95 (1990), p. 419–472, eds. Sporn and Roberts) the BMP (Bone Morphogenetic Protein, see e.g. Rosen and Thies, Growth Factors in Perinatal Development (1993), p. 39–58, eds. Tsang, Lemons and Balistreri) and the inhibin/activin (see e.g. Vale et al., The Physiology of Reproduction, Second Edition, (1994), p. 1861–1878, eds. Knobil and Neill) family. Although the mature parts of members of this family have high amino acid homologies, in particular usually 7 conserved cysteines, their exact functions vary considerably. The TGF-β-like proteins belong to a structural superfamily which all have a cystine knot motif (Cell, vol. 73 (1993), p. 421–424). Further members of this superfamily are proteins from the NGF (nerve growth factor)-/neurotrophin family and PDGF (platelet derived growth factor) family. Individual growth factors often exhibit several functions simultaneously so that their use is of interest for various medical indications.

Some of these multifunctional proteins also have survival promoting effects on neurones in addition to functions such as e.g. regulation of the proliferation and differentiation in many cell types (Roberts and Sporn, Handbook of Experimental Pharmacology 95 (1990), p. 419–472, eds. Sporn and Roberts; Sakurai et al., J. Biol. Chem. 269 (1994), p. 14118–14122). Thus for example trophic effects on embryonic motor and sensory neurones were demonstrated for TGF-β in vitro (Martinou et al., Devl. Brain Res. 52, p. 175–181 (1990) and Chalazonitis et al., Dev. Biol. 152, p. 121–132 (1992)). In addition effects promoting survival were shown on dopaminergic neurones of the midbrain for the proteins TGF-β-1, -2, -3, activin A and GDNF (glial cell line-derived neurotrophic factor), a protein which has structural similarities to TGF-β superfamily members but these effects were not mediated via astrocytes (Krieglstein et al., EMBO J. 14, p. 736–742 (1995)).

WO 93/16099, WO 95/04819 and WO96/01316 disclose the DNA and protein sequences of TGF-β-like proteins in particular of MP52 and MP121. In WO 95/04819 a cartilage and bone-inducing effect is disclosed for MP52.

The occurrence of proteins of the TGF-β superfamily in various tissue stages and development stages corresponds with differences with regard to their exact functions as well as target sites, life-span, requirements for auxiliary factors, necessary cellular physiological environment and/or resistance to degradation.

The object of the present invention is to provide a protein which enables a treatment or prevention of diseases of the nervous system. Of interest are the treatment of disorders or losses of nervous functions. These may be caused by acute pathological states such as in cerebrovascular, inflammatory, infectious, metabolic-like deficiencies or/and deficiencies caused by toxic influences, injuries, tumour growth or operative procedures. In addition disorders or losses of nervous functions can be caused by chronic pathological states such as above all neurodegenerative diseases. Neuropathological situations are also often caused by the ageing of the nervous system.

This object is achieved by the use of biologically active MP52 or/and MP121 for the treatment or/and prevention of diseases of the nervous system or/and for the treatment of neuropathological situations which are caused by the ageing of the nervous system.

It was possible to show with the present invention that MP52 has a positive influence on the survival of dopaminergic neurones (see FIG. 3). However, in contrast to TFG-βs and activin A this influence is mediated at least partially by astrocytes associated with nerve cells (see FIG. 4). Hence MP52 is useful for the treatment or prevention of diseases of the nervous system in particular diseases which affect the brain. In this connection neurodegenerative diseases are of particular interest such as e.g. Parkinson's disease and possibly also diseases such as Alzheimer's or Huntington's Chorea. In addition the application of MP52 promotes the survival of neurones and thus maintains nervous functions. All potential uses are applicable to acute as well as to chronic pathological states and this is also true of the preventive measures. In this case acute pathological states are primarily understood as cerebrovascular, inflammatory, infectious, metabolic-like deficiency phenomena or/and deficiencies caused by toxic influences, injuries, tumour growth or operative procedures.

A chronic pathological state which can be treated within the scope of the invention is for example a neurodegenerative disease. In addition it could also be shown with the present invention that MP52 also has a stimulating influence on neurones of the retina. During the development of the visual system axons migrate from the ganglion cells of the retina to special regions in the brain. Several groups have been able to show that soluble factors which were isolated from the visual regions of the brain can stimulate the ganglion cells in the retina (Nurcombe, V. and Bennett, M. R., Exp. Brain Res. 44, 249–258 (1981), Hyndman, A. G., Adler, R., Dev. Neurosci. 5, 40–53 (1982), Turner, J. E. et al., Dev. Brain Res. 6, 77–83 (1983), Carri, N. G. and Ebendal, T., Dev. Brain Res. 6, 219–229 (1983)). The formation of nerve fiber fascicles which are probably optical axons stemming from the retinal ganglion cells depends on neurotrophic factors.

Experiments with MP52 showed that this protein can also act as a neurotrophic factor in this system.

Thus using freshly isolated tissue cultures of embryonic retina from chicken it could be shown that MP52 significantly promotes the outgrowth of nerve fibers (see FIG. 6 and table 1 for this).

During these experiments it was also possible to show that further members of the TGF-β family also have a stimulating effect. These include in particular also MP121 (WO93/16099 and WO96/01316) which has about the same strong effect as MP52 (see FIG. 6 and table 2 for this).

The activities of MP52 and MP121 can be used to heal diseases of the eye and especially the retina and the optic nerve. In this connection the treatment of injuries to the neuronal layer of the retina and the optic nerve should be emphasized. Such injuries could for example be caused by accidents, inflammation or circulatory disturbances. Applications in retinal transplantations are also advantageous. In addition a healing or alleviation of damage to other brain nerves should also be of importance. In this case emphasis is made for example on the trigeminus (nervus trigeminus) which also innervates parts of the eye. Thus members of the TGF-β family in particular MP52 and MP121 can also be used for corneal transplantations. The growth of the cornea is also influenced by the nerve supply. An application in the case of only segmental damage to the cornea is also conceivable such as those which occur in the case of herpes infections in the eye.

In particular applications for degenerative diseases of the eye surface should be underscored.

In a preferred embodiment of the present invention the following are used as biologically active MP52
  (a) the mature part and optionally further functional parts of the protein sequence shown in SEQ ID NO.1
  (b) parts of the mature protein which essentially have the same activity;
  (c) mature proteins with a modified N-terminus which have essentially the same activity;
  (d) a mature protein or parts thereof which has a different amino acid sequence due to its origin from other vertebrates but essentially retains the same activity.

In another preferred embodiment the following are used as biologically active MP121
  (a) the mature part and optionally further functional parts of the protein sequence shown in SEQ ID NO.3 or 4
  (b) parts of the mature protein which essentially have the same activity;
  (c) mature proteins with a modified N-terminus which have essentially the same activity;
  (d) a mature protein or parts thereof which has a different amino acid sequence due to its origin from other vertebrates but essentially retains the same activity.

Other features and advantages of the invention are indicated by the description of the preferred embodiments and the figures. The sequence protocols and figures are briefly described in the following.

SEQ ID NO.1: shows the complete amino acid sequence of the prepro protein of the human TFG-β protein MP52 which was derived from the nucleotide sequence shown in SEQ ID NO.2 and is already disclosed in WO 95/04819. The start of the mature protein preferably lies in the region of the amino acids 361–400, particularly preferably at amino acid 382.

SEQ ID NO.2: shows the complete nucleotide sequence of the DNA coding for the TFG-β protein MP52 as already disclosed in WO95/04819. The ATG start codon begins with nucleotide 640. The start of the complete mature protein particularly preferably begins after nucleotide 1782. The stop codon begins with nucleotide 2143.

SEQ ID NO.3: shows the complete amino acid sequence of the prepro protein of the human TGF-β protein MP121 which is already disclosed in WO96/01316. The start of the mature protein preferably lies in the region of amino acids 217–240, particularly preferably at amino acid 236 or 237 and most preferably at amino acid 237.

SEQ ID NO.4: shows the complete amino acid sequence of the prepro protein of the TGF-β protein MP121 from the mouse which is also disclosed in WO96/01316. The start of the mature protein lies in the region of the amino acids 217–240 analogously to the human protein, the start of the preferred mature protein is at amino acid 236 or 237.

Figure 1:
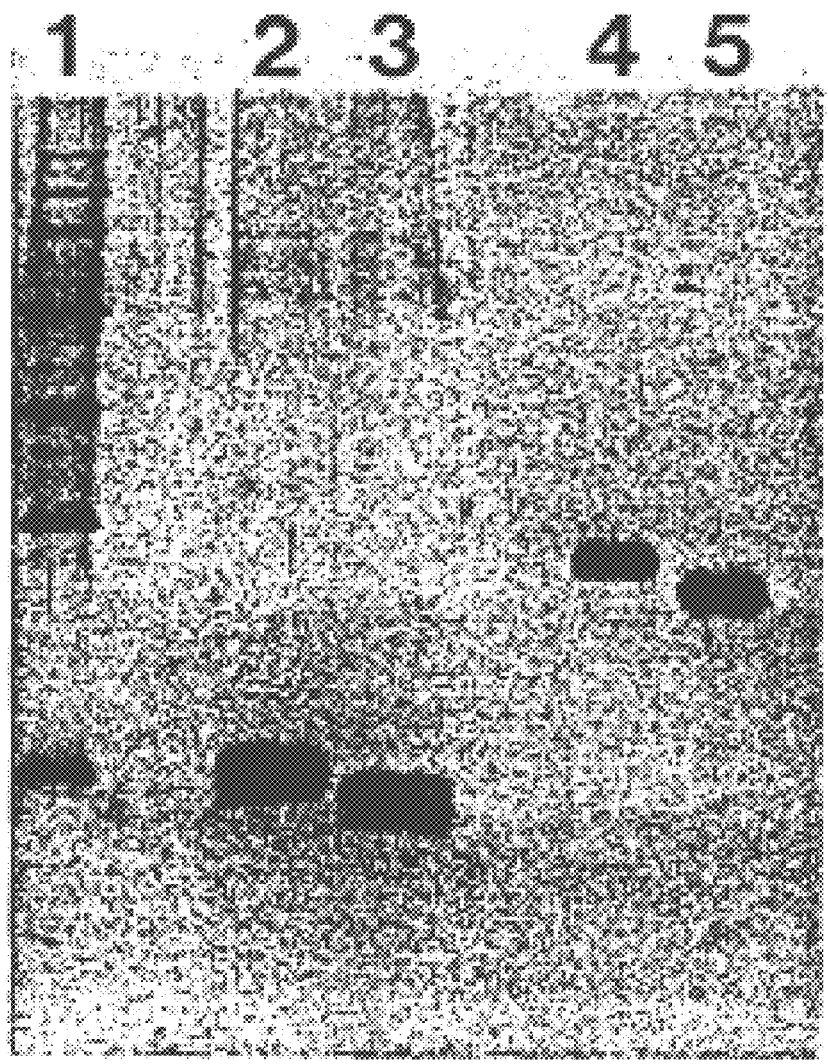
FIG. 1 shows a silver stained gel with mature MP52 expressed in a prokaryotic system with a methionine in front as well as mature MP52 with an additional Histidine tag at the N-terminus before and after refolding.

Within the scope of the present invention the mature part of the MP52 protein comprises amino acid 382 to amino acid 501. In the case of MP121 the mature part preferably comprises amino acid 237 to amino acid 352 of SEQ ID NO.3 or of SEQ ID NO.4. In addition within the scope of the invention shorter or longer functional partial regions of the total protein are also optionally encompassed which have essentially the same biological activity and in particular partial regions which comprise at least the region of the seven conserved cysteines. In the present invention it was possible to show among others that modifications at the N-terminus of the mature protein do not have a major effect on the activity.

MP52 and MP121 proteins are also encompassed which are isolated from other vertebrates since these have essentially the same activities.

On the other hand, in addition to the mature parts of MP52 or MP121, proteins can also include functional signal or/and propeptide parts of other proteins e.g. from proteins with the cystine knot motif (Cell, vol. 73 (1993) p. 421–424) and in particular from other proteins of the TGF-β superfamily e.g. the aforementioned TGF or BMP or activin/inhibin proteins in particular also MP121 and MP52. The corresponding nucleotide sequences can be taken from the aforementioned references and the literature cited therein and/or the EMBL data base or gene bank to the disclosure of which reference is herewith made. In this connection it is important that the correct reading frame for the mature protein is retained. Depending in which host cells expression takes place the presence of another signal sequence or/and of another propeptide part could positively influence the expression. The substitution of propeptide parts by corresponding parts of other proteins is described for example in Mol. Endocrinol. 5 (1991), p. 149–155 and Proc. Natl. Acad. Sci. USA 90 (1993), p. 2905–2909.

A further preferred embodiment of the invention is the use of fusion proteins which have functional derivatives or parts of MP52 or MP121 according to the above definition and as preferably shown in SEQ ID NO.1 or 3 or 4 in particular functional parts of the mature protein and in addition parts of another protein. The other protein in this case can again be a protein with a cystine knot motif which preferably also belongs to the TGF-β superfamily such as e.g. also a combination of MP52 with MP121. However, parts of a completely different protein can also be present e.g. receptor-binding domains of proteins which give the original MP52 or MP121 protein another specificity. Yet a further preferred embodiment of the invention is the use of heterodimeric proteins composed of a monomer of a biologically active MP52 or MP121 according to the above definition and a monomer of a protein from the superfamily of proteins with the cystine-knot motif, preferably a member of the TGF-β superfamily. Similar heterodimeric proteins are described for example in WO 93/09229, EP 0 626 451 A2 and J. Biol. Chem. 265 (1990), p. 13198–13205. The features of the protein can vary depending on the formation of homodimers or hetero-dimers and be relevant for therapeutic applications.

The DNA sequence shown in SEQ ID NO.2, parts thereof or a sequence which codes for chimeric proteins according to the invention can be used for the production of MP52. The expression can take place in eukaryotic and prokaryotic host cells. Suitable expression systems are known to a person skilled in the art and it is easy to establish which minimum part of SEQ ID NO.2 is required in order to obtain an expressed protein which exhibits activity in the stated experiments. The expression systems also include viral systems such as e.g. the baculovirus or the vaccinia virus system. In order to produce an adequate amount of the purified proteins according to the invention from the host cell or/and the cell culture supernatant for use in medical treatment it is possible to use a bacterium such as *E. coli* or Bacillus, a fungus such as yeast, a plant cell such as tobacco or Arabidopsis or an animal vertebrate cell line such as CHO, HuTK, NIH-3T3, COS or Mo cell lines or an insect cell line such as for example *Spodoptera frugiperda* (SF9) or *Trichoplusia ni* (TN368). It is also possible to express in insect larvae such as *Bombyx mori* or *Spodoptera frugiperda* by utilizing recombinant insect viruses such as e.g. *Bombyx mori* nuclear polyhedrosis virus or baculoviruses. Such a system is for example described by Ishida et al. (J. Biochem. 115 (1994), p. 279–285). If the production is in bacteria the protein according to the invention may be present in the form of inclusion bodies. These inclusion bodies are renatured according to known methods in order to obtain the protein in its active form. Within the scope of the invention it could be shown that a renaturation to form a dimeric MP52 is necessary for the activity since monomeric MP52 does not have any activity (see FIG. 3). The same applies to the production of MP121 which is described in detail in WO96/01316.

In order to produce heterodimeric proteins with other members of the cystine knot family both protein monomers are either expressed in the same cell or separately wherein a common renaturation when inclusion bodies are formed would appear to be suitable. If coexpression is in the same cell, viral systems such as e.g. the baculovirus system, the vaccinia virus system are in turn particularly suitable. The production and purification of heterodimeric proteins is known in principle to a person skilled in the art and described for example in WO 93/09229 and EP 0 626 451 A2. Heterodimers can be separated from homodimers by for example using sequential affinity columns with antibodies that are specific in each case for one monomer.

The production of chimeric proteins with other protein parts requires an appropriate modification at the DNA level which is familiar to a person skilled in the art and can be carried out by him (EMBO J. 10 (1991), p. 2105–2110; Cell 69 (1992) p. 329–341; J. Neurosci. 39 (1994), p. 195–210.

In a further preferred embodiment naturally occurring gangliosides, derivatives, salts or artificial analogues thereof are administered in addition to biologically active MP52 or/and MP121 in one of the aforementioned forms. Moreover it is preferred to additionally administer a growth factor. In this case it is preferably a protein from the superfamily of the proteins with the cystine knot motif and is preferably a protein from the TGF-β superfamily, the NGF/neurotrophin family or the PDGF family. Growth factors belonging to the NGF/neurotrophin family are particularly preferred e.g. the growth factors NGF, BDNF, NT-3 or NT4/5 (see also Guidebook to Cytokines and their Receptors, Nicos A., Nicola, A Sambrook and Tooze Publication, Oxford University Press, 1994, page 140–143 and the literature cited therein). Other preferred growth factors are FGF, EGF and glial growth factor. Such combinations can also lead to synergistic effects such as has already been shown for members of the TGF-β superfamily (Ogawa et al., J. Biol. Chem. 267 (1992), 14233–14237 or US 5413989).

If necessary or advantageous it is obvious for a person skilled in the art that common pharmaceutical carrier substances, auxiliary substances, diluents or fillers can be additionally added.

The administration of a composition containing MP52 or/and MP121 is expediently carried out in such a way that the greatest possible effect is achieved and an application near the target area can be of particular advantage. The administration can inter alia be carried out intracerebrally, orally, by injection, by inhalation or as a local external application.

In addition the present invention concerns the use of biologically active MP52 or/and MP121 for the production of a pharmaceutical agent for the treatment or/and prevention of diseases of the nervous system or/and for treating neuropathological situations which are caused by ageing of the nervous system. In this case preferred embodiments and methods of application correspond to the embodiments which have already been described for the previous subject matter of the present invention.

Furthermore the present invention concerns a fusion protein which contains at least parts of the mature region of the sequence of MP52 shown in SEQ ID NO.1 as well as parts at least of another protein from the superfamily of proteins with the cystine knot motif.

Such a fusion protein according to the invention preferably contains (a) the complete mature protein part from SEQ ID NO.1 and optionally further functional parts of the protein sequence shown in SEQ ID NO.1;

(b) the mature part of the protein sequence shown in SEQ ID NO.1 but with a modified N-terminus preferably a methionine placed at the front; or (c) the mature part of the protein sequence shown in SEQ ID NO.1 or parts thereof which is different due to its origin from other vertebrates but essentially retains the same activity.

The production of such fusion proteins as well as examples of suitable proteins from which the non-MP52 protein part can be derived are already described above.

Yet a further subject matter of the present invention is a heterodimeric protein which contains at least a part of the sequence shown in SEQ ID NO.1 of the mature MP52 protein as a monomer as well as a second monomer of another protein from the superfamily of proteins with the cystine knot motif. In this case it is also preferred that the MP52 part (the MP52 monomer) contains (a) the complete mature protein part from SEQ ID NO.1 as well as optionally further functional parts of the protein sequence shown in SEQ ID NO.1;

(b) the mature part of the protein sequence shown in SEQ ID NO.1 but with a modified N-terminus preferably a methionine placed at the front; or (c) the mature part of the protein sequence shown in SEQ ID NO.1 or parts thereof which is different due to its origin from other vertebrates but essentially retains the same activity.

The production of heterodimeric proteins as well as proteins that are suitable as the second monomer have again already been mentioned in the description above.

Yet a further subject matter of the present invention are pharmaceutical agents for the treatment and prevention of diseases of the nervous system or/and for treating neuropathological situations which are caused by ageing of the nervous system and which contain a biologically effective amount of MP52 or/and MP121 as the active substance. The pharmaceutical agent according to the invention preferably contains (a) the mature part and optionally further functional parts of the protein sequence shown in SEQ ID NO.1
(b) parts of the mature protein which essentially have the same activity;
(c) mature proteins with a modified N-terminus which have essentially the same activity;
(d) a mature protein or parts thereof which has a different amino acid sequence due to its origin from other vertebrates but essentially retains the same activity as the biologically active MP52.

In a second preferred form the pharmaceutical agent according to the invention contains (a) the mature part and optionally further functional parts of the protein sequence shown in SEQ ID NO.3 or 4
(b) parts of the mature protein which essentially have the same activity;
(c) mature proteins with a modified N-terminus which have essentially the same activity;
(d) a mature protein or parts thereof which has a different amino acid sequence due to its origin from other vertebrates but essentially retains the same activity as the biologically active MP121.

The possible therapeutic applications of the protein can vary depending on the formation of homodimers or heterodimers with other proteins with a cystine knot motif and in particular TGF-β or NGF proteins as well as by using chimeric proteins. Such structures may also prove suitable for clinical applications and thus they are also a subject matter of the present application.

Thus pharmaceutical compositions which contain heterodimeric proteins and/or fusion proteins according to the invention are also encompassed. A combination of MP52 or MP121 with other proteins of the TGF-β superfamily such as e.g. GDNF, the TGF-βs, BMPs and activins or with proteins of the NGF/neurotrophin family such as e.g. NGF, the neurotrophins such as NT-3, NT-4/5 or BDNF (brain-derived neurotrophic factor) and also growth factors such as FGF (fibroblast growth factor), EGF (epidermal growth factor), glial growth factor, PDGF (platelet-derived growth factor) can also be of advantage in a pharmaceutical composition. Such combinations are also a subject matter of the application.

A composition according to the invention optionally includes pharmaceutically acceptable carrier substances, auxiliary substances, diluents or/and fillers in addition to the active substances.

Such a composition can preferably also include naturally occurring gangliosides, or derivatives, salts or artificial analogues thereof.

In order to treat or prevent nervous diseases, MP52 or MP121 can be injected or administered orally, non-orally, intracerebrally, by inhalation, as a local topical application or by any other common pharmaceutical method. The dose is in the range of 0.1 to 1000 µg/kg body weight.

It is possible to administer biologically active MP52 or/and MP121 or heterodimeric proteins according to the invention and/or chimeric proteins e.g. also via implanted embryonic stem cells which previously have been made to constitutively express proteins according to the invention, in particular of MP52 or MP121, by transfecting suitable DNA elements. In addition it is possible to provide proteins according to the invention in particular biologically active MP52 or MP121 by means of certain viral systems. Thus it is possible to transfect suitable vectors containing the DNA sequence according to the invention in vitro or in vivo into patient cells or to transfect the vectors in vitro into cells and then implant these in a patient.

In addition the application of this pharmaceutical composition is not limited to humans but can also include animals especially domestic animals.

In general the proteins used according to the invention can be used to treat diseases of the nervous system which are associated in some way with the expression of MP52 or MP121 or which respond in any manner to MP52 or MP121 either by increasing the amount of the activity of MP52 or MP121 present or also by suppressing the activity of MP52 or MP121. The activity of MP52 or MP121 can be suppressed by inhibiting the transcription and/or translation for example by antisense nucleic acids known to a person skilled in the art. A further possibility is to bind molecules to MP52 or MP121 receptors which, in contrast to MP52 or MP121, do not trigger signal transmission. Thus within the scope of the invention the receptors for MP52 or MP121 on cells are of interest. In order to find receptors firstly various cell lines can be tested for their binding properties for radioactively labelled MP52 or MP121 ($^{125}$I-MP52 or $^{125}$I-MP121) with subsequent cross-linking. Afterwards it is possible to establish a cDNA library in an expression vector (e.g. obtainable from InVitrogen) of cells which bind MP52 or MP121. Cells which have been transfected with receptor cDNA can then be selected by binding radioactively labelled MP52 or MP121. These methods are known to a person skilled in the art such as those that have been used for isolating activin (Mathews, L. S. & Vale, W. W. Cell 65 (1991) p. 973–982) and TGF-β type II receptor (Lin et al. Cell 68 (1992) p. 775–785). Analogously to the known activin, TGF-β and BMP receptors it can be assumed that the receptor MP52 and MP121 is also a receptor complex which is part of this family so that further methods known to a person skilled in the art such as PCR with degenerate oligonucleotides can be used to find parts of the heteromeric complex. This method has also been used for the activin receptor type I, TGF-β receptors type I and BMP receptors type I (Tsuchida et al. (1993) Proc. Natl. Acad. Sci. USA 90, 11242–11246; Attisano et al. (1993) Cell 75, 671–680; Franzén et al. (1993) Cell 75, 681–692; ten Dijke et al. (1994) J. Biol. Chem. 269, 16985–16988; Koenig et al. (1994) Mol. Cell. Biol. 14, 5961–5974).

It is intended to elucidate the invention by the following examples.

EXAMPLE 1

Eukaryotic Expression and Purification of MP52

Vaccinia viruses were selected for the expression of MP52, the use of which is described in detail and in a manner that can be repeated by a person skilled in the art in Current Protocols in Molecular Biology in chapter 16 unit 16.15–16.18 (Ausubel et al., Greene Publishing Associates and Wiley-Interscience, Wiley & Sons (1989–1995)) abbreviated CP in the following. The cDNA containing the complete coding region for MP52 was cloned into the vector pBP1. The resulting plasmid (pBP1MP52s) was deposited on the May 24th, 1994 at the DSM (deposit number 9217) and used for the production of recombinant Vaccinia viruses as disclosed in WO 95/04819. The expression of MP52 in 143B cells (HuTk, ATCC CRL 8303) after infection with recombinant Vaccinia viruses was carried out as disclosed in WO 95/04819. MP52 was partially purified by means of a heparin column (HiTrap™, Pharmacia #17-0407-01) and a subsequent reversed phase HPLC (C8 column, Aquapore RP300, Applied Biosystems, particle size: 7 μm, pore size: 300 Å) as described in the same disclosure. The fractions containing MP52 were pooled, lyophilized and stored at −80° C.

EXAMPLE 2

Prokaryotic Expression, Purification and Refolding to Form Active MP52

The possible expression of MP52 in *E. coli* is already disclosed in WO93/16099 and WO 95/04819, the expression of mature MP52 also with attached histidines at the N-terminus is also disclosed (WO 95/04819). The additional histidines facilitate the purification of the protein by binding to metal chelate columns. After purification the mature MP52 protein expressed in *E. coli* as a monomer can then be refolded to a dimer. The largest part of the mature region of MP52 (amino acid 383 to 501 in SEQ ID NO.2) with 10 additional amino acids including 6 histidines at the N-terminus (MHHHHHHKLI) (SEQ ID NO.5) was expressed in the prokaryotic vector pBP2. This vector is a pBR322 derivative with ampicillin resistance which additionally contains the T7 promoter from the pBluescript II SK plasmid (Stratagene). The vector furthermore contains a ribosomal binding site after the T7 promoter and a start codon as part of an NdeI restriction cleavage site followed by 6 codons for histidine. Several restriction cleavage sites (Hind III, Eco RI, Xho I, Bam HI, Sma I and Apa I) for the insertion of inserts and stop codons in all three reading frames are followed by a terminator (TØ). Plasmid pBP2MP52His was deposited at the DSM (deposit number: DSM 10028) on the Jun. 2, 1995. The same vector was used for the expression of mature MP52 (amino acid 382 to 501 in SEQ ID NO.1) having only one additional methionine at the N-terminus using the Nde I restriction cleavage site. The plasmid pBP2MP52m was deposited at the DSM (deposit number: DSM 10029) on the Jun. 2, 1995. The expression of MP52 protein with (MP52His) or without (MP52m) a histidine extension can be achieved by simultaneous preparation of T7 RNA polymerase. T7 RNA polymerase can be prepared by various methods such as e.g. a second plasmid containing a gene for T7 RNA polymerase or by infection with phages that code for T7 RNA polymerase or by special bacterial strains which have integrated the gene for T7 RNA polymerase. Using the bacterial strain BL21 (DE3)pLysS (Novagen, #69451-1) and inducing the T7 RNA polymerase according to the manufacturer's instructions with IPTG the MP52 protein with and without a His tag is formed in inclusion bodies from which the proteins can be isolated according to standard methods. Due to the His tag MP52His protein can be purified over metal chelator columns as described for example in Hochuli et al. (BIO/Technology Vol. 6, 1321–1325 (1988)). MP52His and MP52m were purified further by means of reversed phase HPLC. A reversed phase column (Nucleosil 300-7C4 from Macherey-Nagel, cat no. 715023) was used with a flow rate of 2 ml/min and an acetonitrile gradient in 0.1% TFA of 0 to 90% in 100 min. Monomeric MP52His and MP52m begins to elute under these conditions at ca. 35% acetonitrile. The test that this is MP52 protein was in each case carried out using Western blot analysis with MP52 specific antibodies. MP52m (121 amino acids) or MP52His (129 amino acids) exhibit an apparent molecular weight in SDS polyacrylamide gels (15%) of ca. 14 kD (theoretical molecular weight: 13.7 kD) and 15 kD (theoretical molecular weight: 14.8 kD) respectively as can be seen in FIG. 1 after silver staining.

In order to obtain biologically active material, the monomeric MP52 expressed and purified in *E. coli* can be refolded to form a dimeric MP52. This can be carried out according to methods known to a person skilled in the art as described for example by Jaenicke, R. & Rudolph, R. (Protein structure, ed. Creighton, T. E., IRL Press, chapter 9 (1989)). Since the conditions for refolding vary individually for each protein, the conditions for the proteins MP52His and MP52m were tested during the renaturation with regard to solubilization as well as pH values, temperature and redox systems. Typical reagents such as urea and guanidinium chloride proved to be suitable for the solubilization of the purified and lyophilized MP52 proteins. They are preferably solubilized for 2 hours at room temperature in solubilization buffer (6 M guanidinium chloride, 10 mM Tris, 150 mM NaCl, 3 mM DTT pH 8.0) at a final concentration of 2.6 mg MP52His or MP52m per ml. The solubilisate was then added to the renaturation buffer preferably at a final concentration of 150–200 μg MP52His or MP52m per ml.

For the renaturation it turned out that it was advantageous to use high pH ranges (pH 8–10) for refolding to the active MP52 dimer proteins. In this connection the usual buffer systems can be used such as phosphate or Tris buffer containing 1–2 M NaCl and further additives such as EDTA (2–10 mM) and Chaps (15–50 mM). Common redox systems such as oxidized and reduced glutathione (e.g.: 1 mM GSSG, 2 mM GSH) can be used as described in the literature (e.g. Jaenicke, R. & Rudolph, R., Protein structure, ed. Creighton, T. E., IRL Press, chapter 9 (1989)). The refolding can be effectively carried out in a range of 4° C. to room temperature for example for 48 hours. Under such conditions it is possible to convert 50–90% of MP52 proteins into the dimeric form. The said conditions are to be regarded as an example and are not limiting. By varying individual conditions it is possible for a person skilled in the art to convert MP52 with similar efficiency into a dimeric active protein. Analysis of the refolded proteins was carried out by means of reversed phase HPLC and in silver-stained gels. For HPLC MP52 proteins were bound to a column (Aquapore RP-300, 7 μm, Applied Biosystems) at 35% buffer B (buffer A: 0.1% TFA in water; buffer B: 90% acetonitrile, 0.1% TFA) at a flow rate of 0.2 ml/min. The monomeric and dimeric MP52 proteins can be separated from one another (see FIG. 2) in an acetonitrile gradient of 35 to 60% buffer B for 50 min. The proportion of refolded MP52His and MP52m is estimated to be ca. 70–90%. In 15% polyacrylamide gels the dimeric MP52m migrates at about 22 kD (theoretical molecular weight: 27.4 kD) and MP52His at about 24 kD (theoretical molecular weight: 29.6 kD) estimated from a molecular weight marker (see FIG. 1). In this case the histidine tag exhibits no significant influence on the refolding efficiency. When the activity of both proteins is tested by determining the alkaline phosphatase (ALP) activity on ROB-C26 cells as for example disclosed in WO 95/04819 it turns out that MP52His is active despite the modified N-terminus but the activity compared to MP52m is slightly reduced.

EXAMPLE 3

Influence of MP52 on Dopaminergic Neurones

In order to test the influence of MP52 on dopaminergic neurones, neurones were isolated from the base of the mesencephalon of 14 day old rat embryos (E14) according to a method described by Shimoda et al. (Brain Res. 586, 319–331 (1992)). The cells were separated and cultured as described by Krieglstein et al. (Neuroscience 63, 1189–1196 (1994)). The cell density is 200,000 cells/cm$^2$ on polyornithine/laminine coated cover glasses. After culturing for 24 hours and subsequently every three days two thirds of the medium (500 µl) was removed and replaced by fresh medium containing the appropriate additives. The partially purified lyophilized MP52 after heparin-Sepharose and reversed phase HPLC was dissolved in 50% acetonitrile and medium was added. The same was carried out with the refolded and purified MP52His. The final concentration of MP52 and MP52His in the medium is 20 ng/ml (the final concentration of acetonitrile is 0.3%). A comparable amount of purified monomeric MP52His dissolved in 50% acetonitrile was used as a control. The medium control also contains 0.3% acetonitrile. After eight days the cultures were fixed in 4% paraformaldehyde for 10 min at room temperature, the cells were permeabilized with acetone (10 min, −20° C.) and washed with PBS (phosphate buffered saline). After treatment with 1% $H_2O_2$ in PBS, washing and blocking with horse serum they were stained immunocyto-chemically. Tyrosine hydroxylase (TH) is a limiting enzyme in the biosynthesis of dopamine and other catecholamines so that TH can be used as a marker for dopaminergic neurones in the present cultures (cells containing noradrenalin are not isolated). TH was detected by a one hour incubation at 37° C. with a mouse monoclonal antibody against rat TH (diluted 1:200, Boehringer Mannheim) and subsequent detection using the Vectastain ABC kit (Vecto Labs). The TH-positive cells were counted over an area of 0.12 cm$^2$. For the immunocytechemical staining of GFAP (glial fibrillary acidic protein) the fixed cells were permeabilized with acetone (20 min, 20° C.) and washed with PBS (phosphate buffered saline). After incubation with a 1:200 diluted mouse monoclonal antibody against GFAP (Sigma) they were incubated with a peroxidase coupled antibody against the monoclonal mouse antibody. Visualization was carried out according to standard methods by addition of the enzyme substrate DAB (diamino benzidine).

EXAMPLE 4

Investigation of the Transcription of MP52 in Brain and Spinal Cord

In order to establish whether MP52 is transcribed in the brain or/and spinal cord, the total RNA from the spinal cord of rats and from the total brain or individual regions of the brain of mice was isolated according to standard methods and transcribed into cDNA according to methods known to a person skilled in the art. The cDNA which had in each case been obtained from 100 ng RNA was used in a PCR (polymerase chain reaction). The primers used for the amplification (CAACAGCAGCGTGAAGTTGGAG and ACTAATGTCAAACACGTACCTCTG) (SEQ ID NO:6 and 7, respectively) are located on different exons in the case of human genomic DNA so that genomic DNA can be distinguished from cDNA. 0.5 µg genomic mouse DNA was used as a control which also does not yield a PCR fragment like cDNA. The PCR was carried out for 30 cycles (94° C., 54° C., 72° C.) in 50 µl reaction mixture each time (200 µM NTPs each, 30 pmol of each primer, 16.6 mM $(NH_4)_2SO_4$, 67 mM Tris/HCl pH 8.8, 2 mM $MgCl_2$, 6.7 µM EDTA, 10 mM β-mercaptoethanol, 170 µg/ml BSA, 5 U AmpliTaq (Perkin Elmer #N8080160). A third of the PCR products was separated in 4% Agarose gel, transferred onto membranes in a Southern blot and the specificity of the PCR fragments was determined by hybridization with a MP52 probe. It could be shown that MP52 is transcribed in the spinal cord as well as in individual regions of the brain.

EXAMPLE 5

Eukaryotic Expression and Purification of MP121

Vaccinia viruses were selected for the expression of MP121 as for MP52 in example 1. The cDNA containing the complete coding region for MP121 was cloned into the vector pBP1 (the resulting plasmid pBP1MP121 was deposited on the Dec. 1, 1995 at the DSM under the number 9665) and used to produce recombinant vaccinia viruses. When cells such as e.g. NIH-3T3 cells (DSM ACC 59, Swiss mouse embryo) are infected with the recombinant viruses MP121 is expressed. The individual steps are disclosed in detail in WO96/01316. In the course of the expression experiments other cell lines were also tested. In this case it surprisingly turns out that in some cell lines significant amounts of monomeric MP121 is formed in addition to dimeric MP121. Since this monomer migrates more rapidly when analyzed in a polyacrylamide gel (with subsequent detection by Western blot analysis) than the monomer obtained by reduction of the dimer, this has to be a folded monomeric MP121 having a globular structure. The expression of MP121 in HepG2 cells (hepatocellular carcinoma, human, ATCC HB8065) is shown as an example in FIG. 5. Since it was in the meantime possible to show by means of Northern blot analysis that MP121 is naturally expressed in HepG2 (hepatocyte cell line from the liver), it can be assumed that the monomeric form of MP121 also is of physiological importance. Monomeric MP121 appears in significant amounts in addition to dimeric MP121 for example also in Mv1Lu (NBL-7, lung, mink, ATCC CCL 64) or Hela (epithelial carcinoma, cervix human, ATCC CCL 2).

In expression experiments of MP121 using the baculovirus system in insect larvae (*Trichoplusia ni*) the dimeric form was found in the haemolymph.

Partial purification of MP121 from the cell culture supernatant was carried out by means of phenyl-Sepharose and reversed phase HPLC as described in WO96/01316. The corresponding amount of cell culture supernatant after infection with wild-type viruses (wt) was processed in parallel as a control using the same procedure. In experiments for the improvement of the purification it was possible to show that an alternating use of mobile solvents which contain TFA (trifluoroacetic acid) or HFBA (heptafluorobutyric acid) combined with modified gradient slopes could significantly increase the degree of purification of MP121. For this a column (Aquapore RP-300, Applied Biosystems, particle size: 7 µm) was for example firstly eluted at a flow rate of 0.2 ml/min with 0.1% TFA (1.36% acetonitrile per min) in the mobile solvent, then a column was eluted with 0.2% HFBA (0.23% acetonitrile per min) in the mobile solvent and finally a column was again eluted with 0.1% TFA (0.23% acetonitrile per min) in the mobile solvent. The eluted fractions that contain MP121 can be combined after each run, lyophilized and then resuspended in 0.1% TFA/ H$_2$O for application to the new column. Finally the lyophilized samples were stored at −70° C. until use. The amounts were estimated in Western blot analyses compared to MP121m (amino acid 237 to 352 in SEQ ID NO.3 having an additional methionine at the N-terminus) which had been prepared in *E. coli* similar to MP52 but using the strain HMS 174 (DE3) (Novagen #69453). The purification was carried out according to standard methods from inclusion bodies with subsequent washing of the inclusion bodies with 2 M guanidinium chloride/HCl in 20 mM Tris pH 8.0 (under sonification) and resuspension in 6 M guanidinium chloride/ HCl in 20 mM Tris pH 8.0 with subsequent purification by means of reversed phase HPLC according to standard methods.

EXAMPLE 6

Influence of MP52 and MP121 on Neurones of the Retina

In order to examine the influence of MP52 and MP121 in a different system, tissue cultures were isolated from the retina of chicken embryos. The method for isolating disk-shaped tissue samples from the retina of about the same size is described in detail by Carri, N. G. and Ebendal, T. (Dev. Brain Res., Vol. 6 (1983), 219–229), Carri, N. G. and Ebendal, T. (Anat. Rec., Vol. 214 (1986), p. 226–229) and Carri, N. G. et al. (J. Neurosci. Res. Vol. 19 (1988), p. 428–439).

In these experiments the stimulation of the outgrowth of nerve fibers from embryonic retinal explants is measured in vitro on a collagen matrix. In brief, portions of tissue are taken from the retina of chicken embryos (white Leghorn, 6th day of embryonic development) using a glass capillary and mesenchymal cells were removed by repeatedly washing the pigment epithelium of the retina. The tissue particles treated in this manner were transferred to culture dishes coated with collagen and incubated overnight (37.5° C. 5% CO$_2$). Subsequently the appropriate factors or controls were added and the cultures were incubated further. The dimeric MP52m was used at various concentrations for MP52 as described in example 2. Monomeric MP52 which until then had shown no activity in any experiment, was used as a negative control at the appropriate concentrations. For MP121 the partially purified material described in example 5 was used at various concentrations after phenyl-Sepharose and reversed phase HPLC. The material isolated accordingly after wild-type infection was used as a control. As an independent control the explants were kept in a culture medium containing a small amount of bovine serum albumin.

The proteins were dissolved in an aqueous buffer or 50% acetonitrile and diluted further in culture medium to final concentrations of 1.25 ng/ml, 12.5 ng/ml, 25 ng/ml, 50 ng/ml, 100 ng/ml, 200 ng/ml. The type of dissolution had no influence on the result.

After four days in culture the maximum length of the leading nerve fibers was measured in a dark field under a microscope. MP52 as well as MP121 dose-dependently stimulate the outgrowth of neurites as shown in table 1 and 2. MP52 has a maximum activity in the range of 25–100 ng/ml and MP121 exhibits maximum activity in the range of ca. 25 ng/ml which corresponds to a real fiber length of 1.3–1.7 mm or 1.7 mm compared to 0.2 mm for the negative control. Monomeric MP52 and the wild-type control exhibited no stimulation that exceeded the negative control.

TABLE 1

| dimeric MP52m (ng/ml) | Length (units) | Mean ± SEM |
| --- | --- | --- |
| 1.25 | 15/9/4/13 | 10.2 ± 2.4 |
| 12.5 | 25/18/10/21 | 18.5 ± 3.1 |
| 25 | 74/38/48/47/27/30 | 44.0 ± 6.9 |
| 50 | 62/65/52/51/50/62 | 57.0 ± 2.4 |
| 100 | 26/33/61/70/57/61 | 51.5 ± 7.3 |
| 200 | 10/13/11/9 | 10.7 ± 0.8 |

Table 1: Length of the retinal neurites after 4 days culture under the influence of various concentrations of MP52. The length of the neurites of the controls that only contained culture medium was 5.5/8/10/11/4.8/7 units with a mean of 7.7 units (SEM 1.0). The length of the neurites of the controls containing monomeric MP52m (equal concentrations to dimeric MP52m) yielded on average the same lengths as the controls that only contained culture medium. One unit corresponds to a real scale of 0.03 mm in the culture dish.

TABLE 2

| MP121 (ng/ml) | Length (units) | Mean ± SEM |
| --- | --- | --- |
| 1.25 | 7/12/5/6 | 7.5 ± 1.5 |
| 12.5 | 19/20/13/26 | 19.5 ± 2.6 |
| 25 | 50/52/60/71/65/53 | 58.5 ± 3.4 |
| 50 | 37/32/48/41/36/20 | 35.6 ± 3.8 |
| 100 | 21/8/19/18 | 16.5 ± 2.9 |
| 200 | 11/8/12/10 | 10.2 ± 0.8 |

Table 2: Length of retinal neurites after 4 days culture under the influence of various concentrations of MP121. The length of the neurites of the control containing cell culture supernatant from the wild-type infection that was purified in parallel yielded an average the same lengths as the control that only contained culture medium (see text for table 1.) One unit corresponds to a real scale of 0.03 mm in the culture dish.

DETAILED DESCRIPTION OF THE FIGURES

FIG. 1: Silver-stained 15% polyacrylamide gel with 0.2 μg MP52His (lane 2 and 4) or 0.2 μg MP52m (lane 3 and 5) after purification of the monomeric form (lane 2 and 3) and after folding to the dimeric active protein and separation of residual monomers by means of HPLC (lane 4 and 5). The molecular weight marker (15 kD, 25 kD, 35 kD, 50 kD, 75 kD, 100 kD, 150 kD) in lane 1 is from Novagen (#69149-1).

Figure 2:
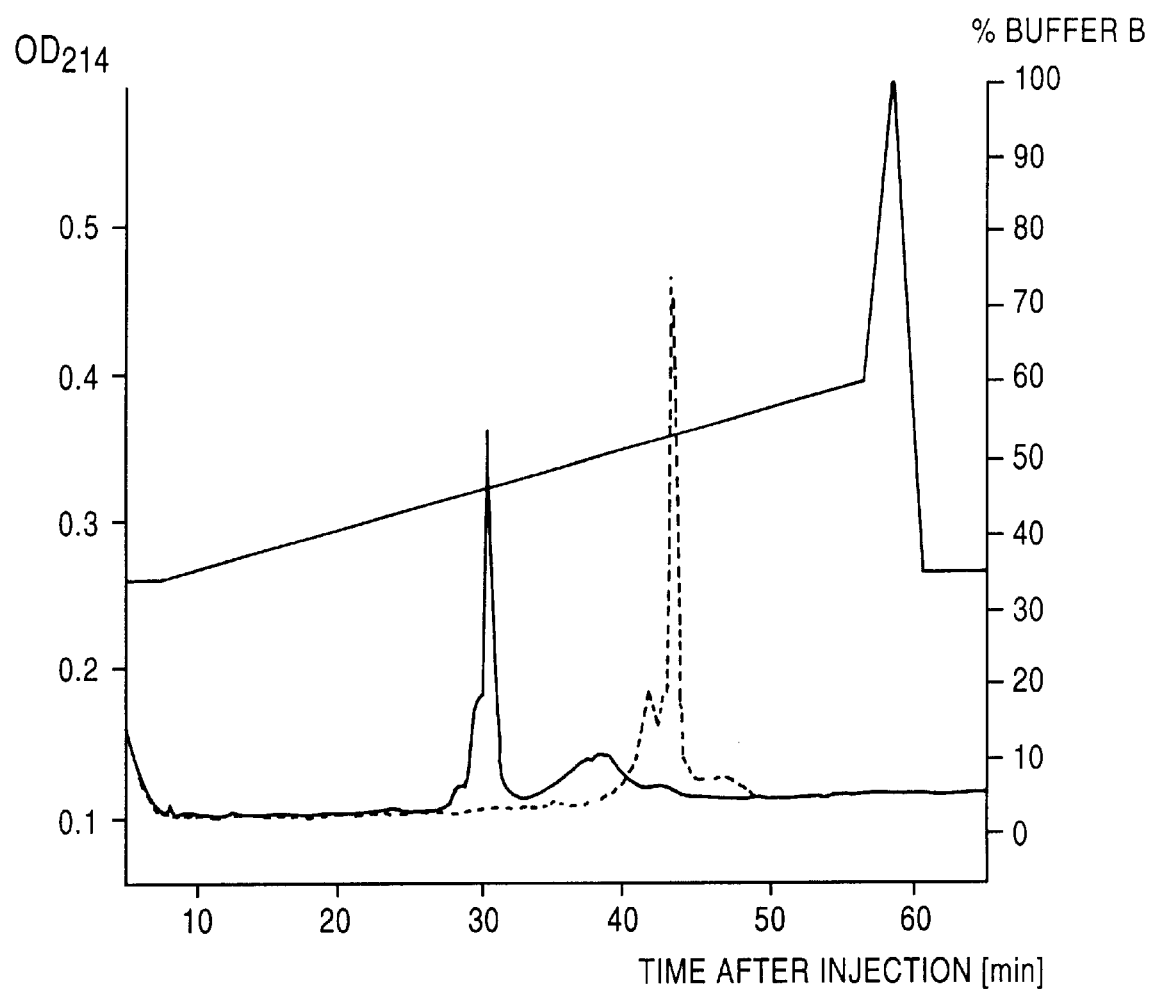
FIG. 2 shows a chromatogram to separate dimeric and monomeric mature MP52 with a modified N-terminus after refolding.

FIG. 2: The chromatogram shows the migration characteristics of solubilized monomeric MP52His (•••) and the separation of dimeric MP52His from the residual monomeric forms after renaturation (—) on reversed phase HPLC. Dimeric MP52His elutes earlier than the monomeric form under the selected conditions. The acetonitrile gradient is also shown in relation to % buffer B.

Figure 3:
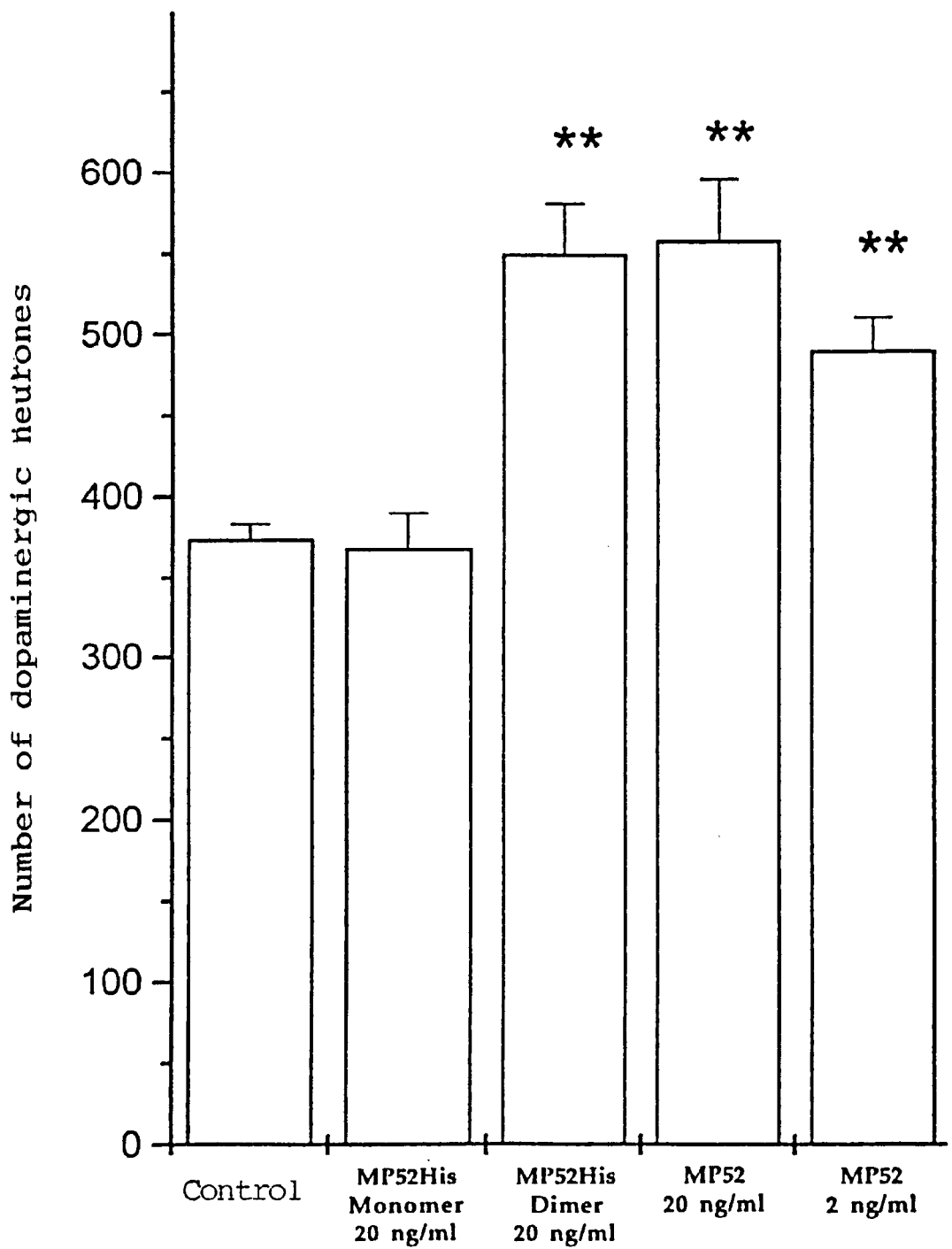
FIG. 3 shows a positive influence on the survival of dopaminergic neurones by treatment with partially purified MP52 from a eukaryotic expression system as well as purified refolded mature MP52 with a modified N-terminus from a prokaryotic expression system.

FIG. 3: Number of surviving TH-immunoreactive dopaminergic neurones after isolation from the midbrain of rat embryos (E14) and 8 days culture. Apart from the control with untreated neurones (medium containing 0.3% acetonitrile) it shows the effect of adding 20 ng/ml purified monomeric MP52His from the expression in *E. coli* (MP52His monomer), 20 ng/ml purified MP52His from the expression in *E. coli* after renaturation to the dimeric protein (MP52His dimer) and 20 ng/ml and 2 ng/ml partially purified MP52 from the expression in vaccinia viruses (MP52). The mean value±SEM from a triple determination is shown.

Figure 4:
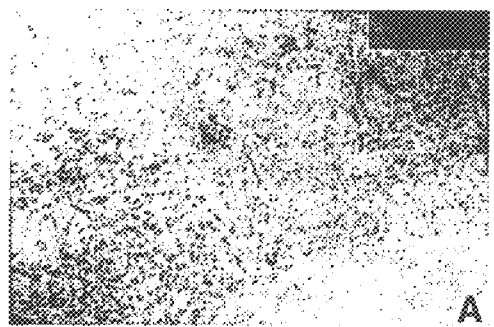
FIG. 4 shows that the survival-promoting effect of MP52 on dopaminergic neurones is at least partially due to an increase in the number of astrocytes.
Figure 4:
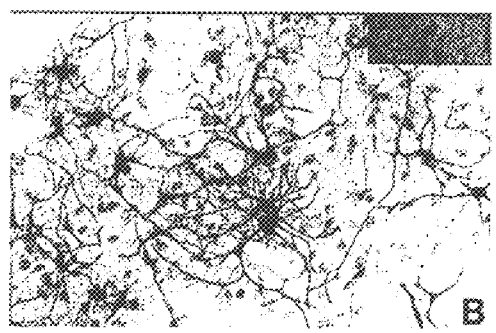
Figure 4:
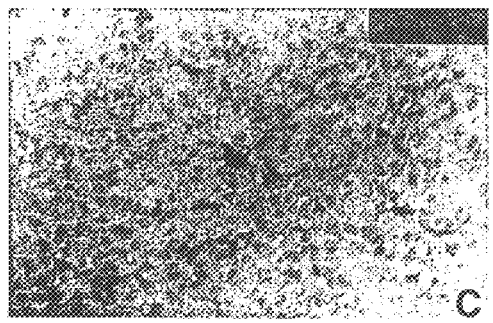
Figure 4:
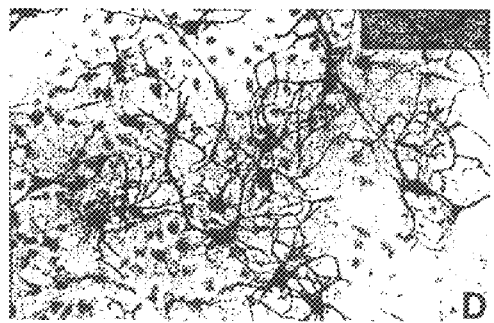
Figure 4:
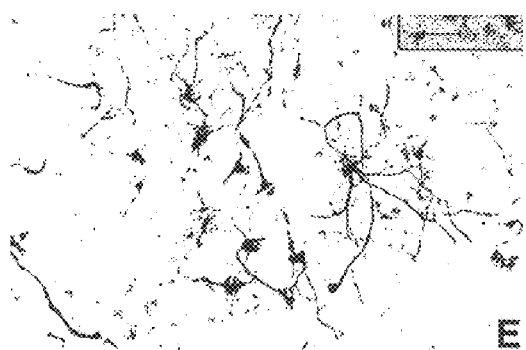
Figure 4:

FIG. 4: Photograph of cells after isolation from the midbrain of rat embryos (E14) after 8 days culture and staining the GFAPs (glial fibrillary acidic proteins). It shows the effect of 20 ng/ml purified monomeric MP52His (A) from the expression in E. coli, 20 ng/ml purified dimeric MP52His (B) from the expression in E. coli after renaturation, untreated cells (C, medium containing 0.3% acetonitrile as a control), 20 ng/ml (D) and 2 ng/ml (E) partially purified MP52 from the expression in vaccinia viruses and 2 ng/ml TGF-β 3 (F).

In each case a representative section at a 400-fold enlargement was photographed in a microscope (Axiophot) with interference contrast. The length of the line (—) corresponds to 25 μm.

Figure 5:
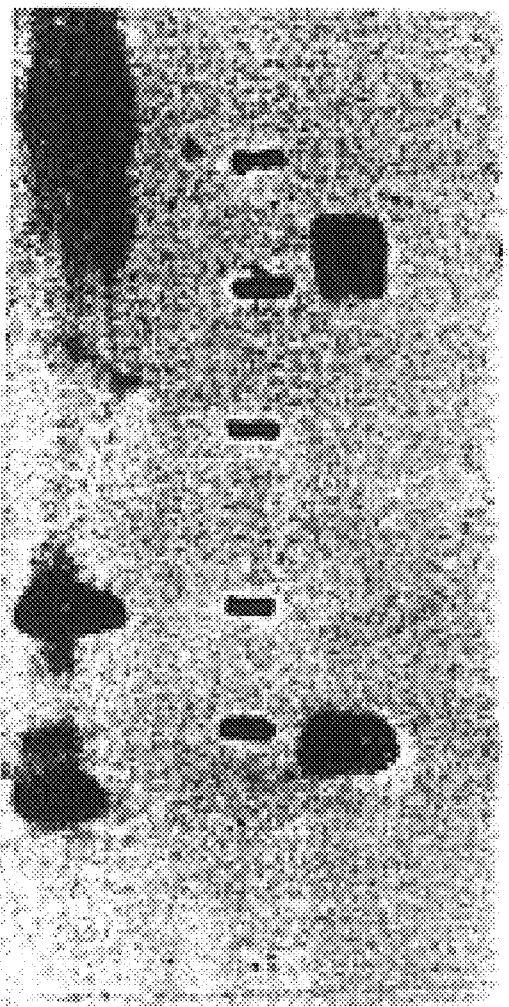
FIG. 5 shows a Western blot with rabbit antibodies against MP121 which was synthesized with the aid of a vaccinia virus expression system in HepG2 cells.

FIG. 5: Western blot with rabbit antibodies against MP121

1: Cell culture supernatant of Hep-G2 cells after infection with recombinant vaccinia viruses (with inserted MP121 cDNA) under non-reducing conditions 2: cell culture supernatant of Hep-G2 cells after infection with wild-type vaccinia viruses under non-reducing conditions 3: prestained protein molecular weight marker (drawn diagrammatically) having apparent molecular weights of 15.5/18.2/27.8/43.8/71.5 kD (Gibco BRL #26041-020)

Figure 6:
FIG. 6 shows the stimulating effect of purified MP52 and MP121 on the growing out of nerve fibers from the embryonic retina.
Figure 6:
Figure 6:

4: cell culture supernatant of Hep-G2 cells after infection with recombinant vaccinia viruses (with inserted MP121 cDNA) under reducing conditions 5: cell culture supernatant of Hep-G2 cells after infection with wild-type vaccinia viruses under reducing conditions FIG. 6: Outgrowth of nerve fibers from embryonic chicken retina after 4 days in tissue culture. Microscopic picture of living cultures in a dark field.

A: monomeric MP52m (5 ng/ml) purified from inclusion bodies of E. coli

B: dimeric MP52m (5 ng/ml) purified from inclusion bodies of E. coli and refolded to the native dimeric protein C: MP121 (5 ng/ml) purified from a cell culture supernatant after expression with the aid of the Vaccinia system on NIH3T3 cells.

What is claimed is:

1. A method for increasing survival of dopaminergic neurons in a human patient with an acute or a chronic neurological disease, comprising administering an amount of MP52 effective to increase the survival of dopaminergic neurons to said patient, wherein said MP52 is selected from the group consisting of
   a) an amino acid sequence comprising residues 1 to 501 of SEQ ID NO: 1;
   b) an amino acid sequence encoded by nucleotide residues 640 to 2142 of SEQ ID NO: 2;
   c) an amino acid sequence comprising residues starting from 361 to 400 through 501 of SEQ ID NO: 1;
   d) an amino acid sequence comprising amino acid residues 382 to 501 of SEQ ID NO: 1; and/or
   e) an amino acid sequence according to (c), wherein the N-terminus is modified by addition of a methionine residue and/or a histidine tag.

2. The method of claim 1, further comprising administering to said patient at least one ganglioside or a salt thereof.

3. The method of claim 1, further comprising administering a protein from a TGF-β superfamily, NGF/neurotrophin family or PDGF family of proteins to said patient.

4. The method of claim 3, wherein said protein is selected from the group consisting of TGF-β, BMP, activin, GDNF, NGF, BDNF, NT3, NT4/5 and MP121.

5. The method of claim 3, wherein the neurological disease is Parkinson's disease.

6. The method of claim 1, further comprising administering a growth factor other than MP52 to said patient.

7. The method of claim 6, wherein said growth factor is FGF, EGF or glial growth factor.

8. The method of claim 6, wherein the neurological disease is Parkinson's disease.

9. The method of claim 1, wherein said MP52 is administered intracerebrally or by injection.

10. The method of claim 1, wherein the neurological disease is Parkinson's disease.

* * * * *

UNITED STATES PATENT AND TRADEMARK OFFICE
CERTIFICATE OF CORRECTION

| | | |
|---|---|---|
| PATENT NO. | : 6,531,450 B2 | Page 1 of 1 |
| DATED | : March 11, 2003 | |
| INVENTOR(S) | : Gertrud Hötten et al. | |

It is certified that error appears in the above-identified patent and that said Letters Patent is hereby corrected as shown below:

<u>Title page,</u>
Item [30], Foreign Application Priority Data, change the date from "Dec. 7, 1995" to -- July 12, 1995 --.

Signed and Sealed this

Twenty-fifth Day of November, 2003

JAMES E. ROGAN
*Director of the United States Patent and Trademark Office*

SEQUENCE LISTING

```
<160> NUMBER OF SEQ ID NOS: 7

<210> SEQ ID NO 1
<211> LENGTH: 501
<212> TYPE: PRT
<213> ORGANISM: Homo sapiens

<400> SEQUENCE: 1

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
            20                  25                  30

Gln Arg Pro Gln Gly Thr Arg Pro Gly Leu Ala Lys Ala Glu Ala Lys
        35                  40                  45

Glu Arg Pro Pro Leu Ala Arg Asn Val Phe Arg Pro Gly Gly His Ser
    50                  55                  60

Tyr Gly Gly Gly Ala Thr Asn Ala Asn Ala Arg Ala Lys Gly Gly Thr
65                  70                  75                  80

Gly Gln Thr Gly Gly Leu Thr Gln Pro Lys Lys Asp Glu Pro Lys Lys
                85                  90                  95

Leu Pro Pro Arg Pro Gly Gly Pro Glu Pro Lys Pro Gly His Pro Pro
            100                 105                 110

Gln Thr Arg Gln Ala Thr Ala Arg Thr Val Thr Pro Lys Gly Gln Leu
        115                 120                 125

Pro Gly Gly Lys Ala Pro Pro Lys Ala Gly Ser Val Pro Ser Ser Phe
    130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
                180                 185                 190

Lys Leu Glu Ala Gly Leu Ala Asn Thr Ile Thr Ser Phe Ile Asp Lys
            195                 200                 205
```

-continued

```
Gly Gln Asp Asp Arg Gly Pro Val Val Arg Lys Gln Arg Tyr Val Phe
    210                 215                 220
Asp Ile Ser Ala Leu Glu Lys Asp Gly Leu Leu Gly Ala Glu Leu Arg
225                 230                 235                 240
Ile Leu Arg Lys Lys Pro Ser Asp Thr Ala Lys Pro Ala Ala Pro Gly
                245                 250                 255
Gly Gly Arg Ala Ala Gln Leu Lys Leu Ser Ser Cys Pro Ser Gly Arg
            260                 265                 270
Gln Pro Ala Ser Leu Leu Asp Val Arg Ser Val Pro Gly Leu Asp Gly
        275                 280                 285
Ser Gly Trp Glu Val Phe Asp Ile Trp Lys Leu Phe Arg Asn Phe Lys
    290                 295                 300
Asn Ser Ala Gln Leu Cys Leu Glu Leu Glu Ala Trp Glu Arg Gly Arg
305                 310                 315                 320
Ala Val Asp Leu Arg Gly Leu Gly Phe Asp Arg Ala Ala Arg Gln Val
                325                 330                 335
His Glu Lys Ala Leu Phe Leu Val Phe Gly Arg Thr Lys Lys Arg Asp
            340                 345                 350
Leu Phe Phe Asn Glu Ile Lys Ala Arg Ser Gly Gln Asp Asp Lys Thr
        355                 360                 365
Val Tyr Glu Tyr Leu Phe Ser Gln Arg Arg Lys Arg Arg Ala Pro Leu
    370                 375                 380
Ala Thr Arg Gln Gly Lys Arg Pro Ser Lys Asn Leu Lys Ala Arg Cys
385                 390                 395                 400
Ser Arg Lys Ala Leu His Val Asn Phe Lys Asp Met Gly Trp Asp Asp
                405                 410                 415
Trp Ile Ile Ala Pro Leu Glu Tyr Glu Ala Phe His Cys Glu Gly Leu
            420                 425                 430
Cys Glu Phe Pro Leu Arg Ser His Leu Glu Pro Thr Asn His Ala Val
        435                 440                 445
Ile Gln Thr Leu Met Asn Ser Met Asp Pro Glu Ser Thr Pro Pro Thr
    450                 455                 460
Cys Cys Val Pro Thr Arg Leu Ser Pro Ile Ser Ile Leu Phe Ile Asp
465                 470                 475                 480
Ser Ala Asn Asn Val Val Tyr Lys Gln Tyr Glu Asp Met Val Val Glu
                485                 490                 495
Ser Cys Gly Cys Arg
            500

<210> SEQ ID NO 2
<211> LENGTH: 2703
<212> TYPE: DNA
<213> ORGANISM: Homo sapiens
<220> FEATURE:
<221> NAME/KEY: CDS
<222> LOCATION: (640)..(2142)
<223> OTHER INFORMATION:

<400> SEQUENCE: 2
ccatggcctc gaaagggcag cggtgatttt tttcacataa atatatcgca cttaaatgag      60
tttagacagc atgacatcag agagtaatta aattggtttg ggttggaatt ccgtttccaa     120
ttcctgagtt caggtttgta aaagattttt ctgagcacct gcaggcctgt gagtgtgtgt     180
gtgtgtgtgt gtgtgtgtgt gtgtgtgtga agtattttca ctggaaagga ttcaaaacta     240
gggggaaaaa aaaactggag cacacaggca gcattacgcc attcttcctt cttggaaaaa     300
```

-continued

```
tccctcagcc ttatacaagc ctccttcaag ccctcagtca gttgtgcagg agaaaggggg        360
cggttggctt tctcctttca agaacgagtt attttcagct gctgactgga gacggtgcac        420
gtctggatac gagagcattt ccactatggg actggataca acacacacc cggcagactt         480 caagagtctc agactgagga gaaagccttt ccttctgctg ctactgctgc tgccgctgct        540
tttgaaagtc cactcctttc atggtttttc ctgccaaacc agaggcacct ttgctgctgc        600
cgctgttctc tttggtgtca ttcagcggct ggccagagg atg aga ctc ccc aaa           654
                                            Met Arg Leu Pro Lys
                                             1               5 ctc ctc act ttc ttg ctt tgg tac ctg gct tgg ctg gac ctg gaa ttc          702
Leu Leu Thr Phe Leu Leu Trp Tyr Leu Ala Trp Leu Asp Leu Glu Phe
             10                  15                  20 atc tgc act gtg ttg ggt gcc cct gac ttg ggc cag aga ccc cag ggg          750
Ile Cys Thr Val Leu Gly Ala Pro Asp Leu Gly Gln Arg Pro Gln Gly
             25                  30                  35 acc agg cca gga ttg gcc aaa gca gag gcc aag gag agg ccc ccc ctg          798
Thr Arg Pro Gly Leu Ala Lys Ala Glu Ala Lys Glu Arg Pro Pro Leu
         40                  45                  50 gcc cgg aac gtc ttc agg cca ggg ggt cac agc tat ggt ggg ggg gcc          846
Ala Arg Asn Val Phe Arg Pro Gly Gly His Ser Tyr Gly Gly Gly Ala
     55                  60                  65 acc aat gcc aat gcc agg gca aag gga ggc acc ggg cag aca gga ggc          894
Thr Asn Ala Asn Ala Arg Ala Lys Gly Gly Thr Gly Gln Thr Gly Gly
 70                  75                  80                  85 ctg aca cag ccc aag aag gat gaa ccc aaa aag ctg ccc ccc aga ccg          942
Leu Thr Gln Pro Lys Lys Asp Glu Pro Lys Lys Leu Pro Pro Arg Pro
                 90                  95                 100 ggc ggc cct gaa ccc aag cca gga cac cct ccc caa aca agg cag gct          990
Gly Gly Pro Glu Pro Lys Pro Gly His Pro Pro Gln Thr Arg Gln Ala
            105                 110                 115 aca gcc cgg act gtg acc cca aaa gga cag ctt ccc gga ggc aag gca         1038
Thr Ala Arg Thr Val Thr Pro Lys Gly Gln Leu Pro Gly Gly Lys Ala
        120                 125                 130 ccc cca aaa gca gga tct gtc ccc agc tcc ttc ctg ctg aag aag gcc         1086
Pro Pro Lys Ala Gly Ser Val Pro Ser Ser Phe Leu Leu Lys Lys Ala
    135                 140                 145 agg gag ccc ggg ccc cca cga gag ccc aag gag ccg ttt cgc cca ccc         1134
Arg Glu Pro Gly Pro Pro Arg Glu Pro Lys Glu Pro Phe Arg Pro Pro
150                 155                 160                 165 ccc atc aca ccc cac gag tac atg ctc tcg ctg tac agg acg ctg tcc         1182
Pro Ile Thr Pro His Glu Tyr Met Leu Ser Leu Tyr Arg Thr Leu Ser
                170                 175                 180 gat gct gac aga aag gga ggc aac agc agc gtg aag ttg gag gct ggc         1230
Asp Ala Asp Arg Lys Gly Gly Asn Ser Ser Val Lys Leu Glu Ala Gly
            185                 190                 195 ctg gcc aac acc atc acc agc ttt att gac aaa ggg caa gat gac cga         1278
Leu Ala Asn Thr Ile Thr Ser Phe Ile Asp Lys Gly Gln Asp Asp Arg
        200                 205                 210 ggt ccc gtg gtc agg aag cag agg tac gtg ttt gac att agt gcc ctg         1326
Gly Pro Val Val Arg Lys Gln Arg Tyr Val Phe Asp Ile Ser Ala Leu
    215                 220                 225 gag aag gat ggg ctg ctg ggg gcc gag ctg cgg atc ttg cgg aag aag         1374
Glu Lys Asp Gly Leu Leu Gly Ala Glu Leu Arg Ile Leu Arg Lys Lys
230                 235                 240                 245 ccc tcg gac acg gcc aag cca gcg gcc ccc gga ggc ggg cgg gct gcc         1422
Pro Ser Asp Thr Ala Lys Pro Ala Ala Pro Gly Gly Gly Arg Ala Ala
                250                 255                 260
```

| | |
|---|---|
| cag ctg aag ctg tcc agc tgc ccc agc ggc cgg cag ccg gcc tcc ttg<br>Gln Leu Lys Leu Ser Ser Cys Pro Ser Gly Arg Gln Pro Ala Ser Leu<br>     265                    270                   275 | 1470 |
| ctg gat gtg cgc tcc gtg cca ggc ctg gac gga tct ggc tgg gag gtg<br>Leu Asp Val Arg Ser Val Pro Gly Leu Asp Gly Ser Gly Trp Glu Val<br>         280                   285              290 | 1518 |
| ttc gac atc tgg aag ctc ttc cga aac ttt aag aac tcg gcc cag ctg<br>Phe Asp Ile Trp Lys Leu Phe Arg Asn Phe Lys Asn Ser Ala Gln Leu<br>     295                    300                   305 | 1566 |
| tgc ctg gag ctg gag gcc tgg gaa cgg ggc agg gcc gtg gac ctc cgt<br>Cys Leu Glu Leu Glu Ala Trp Glu Arg Gly Arg Ala Val Asp Leu Arg<br>310                 315                   320                   325 | 1614 |
| ggc ctg ggc ttc gac cgc gcc gcc cgg cag gtc cac gag aag gcc ctg<br>Gly Leu Gly Phe Asp Arg Ala Ala Arg Gln Val His Glu Lys Ala Leu<br>         330                   335              340 | 1662 |
| ttc ctg gtg ttt ggc cgc acc aag aaa cgg gac ctg ttc ttt aat gag<br>Phe Leu Val Phe Gly Arg Thr Lys Lys Arg Asp Leu Phe Phe Asn Glu<br>     345                    350                   355 | 1710 |
| att aag gcc cgc tct ggc cag gac gat aag acc gtg tat gag tac ctg<br>Ile Lys Ala Arg Ser Gly Gln Asp Asp Lys Thr Val Tyr Glu Tyr Leu<br>         360                   365              370 | 1758 |
| ttc agc cag cgg cga aaa cgg cgg gcc cca ctg gcc act cgc cag ggc<br>Phe Ser Gln Arg Arg Lys Arg Arg Ala Pro Leu Ala Thr Arg Gln Gly<br>375                 380                   385 | 1806 |
| aag cga ccc agc aag aac ctt aag gct cgc tgc agt cgg aag gca ctg<br>Lys Arg Pro Ser Lys Asn Leu Lys Ala Arg Cys Ser Arg Lys Ala Leu<br>390                 395                   400                   405 | 1854 |
| cat gtc aac ttc aag gac atg ggc tgg gac gac tgg atc atc gca ccc<br>His Val Asn Phe Lys Asp Met Gly Trp Asp Asp Trp Ile Ile Ala Pro<br>         410                   415              420 | 1902 |
| ctt gag tac gag gct ttc cac tgc gag ggg ctg tgc gag ttc cca ttg<br>Leu Glu Tyr Glu Ala Phe His Cys Glu Gly Leu Cys Glu Phe Pro Leu<br>     425                    430                   435 | 1950 |
| cgc tcc cac ctg gag ccc acg aat cat gca gtc atc cag acc ctg atg<br>Arg Ser His Leu Glu Pro Thr Asn His Ala Val Ile Gln Thr Leu Met<br>440                 445                   450 | 1998 |
| aac tcc atg gac ccc gag tcc aca cca ccc acc tgc tgt gtg ccc acg<br>Asn Ser Met Asp Pro Glu Ser Thr Pro Pro Thr Cys Cys Val Pro Thr<br>     455                    460               465 | 2046 |
| cgg ctg agt ccc atc agc atc ctc ttc att gac tct gcc aac aac gtg<br>Arg Leu Ser Pro Ile Ser Ile Leu Phe Ile Asp Ser Ala Asn Asn Val<br>470                 475                   480                   485 | 2094 |
| gtg tat aag cag tat gag gac atg gtc gtg gag tcg tgt ggc tgc agg<br>Val Tyr Lys Gln Tyr Glu Asp Met Val Val Glu Ser Cys Gly Cys Arg<br>         490                   495              500 | 2142 |
| tagcagcact ggccctctgt cttcctgggt ggcacatccc aagagcccct tcctgcactc | 2202 |
| ctggaatcac agaggggtca ggaagctgtg gcaggagcat ctacacagct tgggtgaaag | 2262 |
| gggattccaa taagcttgct cgctctctga gtgtgacttg ggctaaaggc cccctttat | 2322 |
| ccacaagttc ccctggctga ggattgctgc ccgtctgctg atgtgaccag tggcaggcac | 2382 |
| aggtccaggg agacagactc tgaatgggac tgagtcccag gaaacagtgc tttccgatga | 2442 |
| gactcagccc accatttctc ctcacctggg ccttctcagc ctctggactc tcctaagcac | 2502 |
| ctctcaggag agccacaggt gccactgcct cctcaaatca catttgtgcc tggtgacttc | 2562 |
| ctgtccctgg gacagttgag aagctgactg ggcaagagtg ggagagaaga ggagagggct | 2622 |
| tggatagagt tgaggagtgt gaggctgtta gactgttaga tttaaatgta tattgatgag | 2682 |
| ataaaaagca aaactgtgcc t | 2703 |

-continued

```
<210> SEQ ID NO 3
<211> LENGTH: 352
<212> TYPE: PRT
<213> ORGANISM: Homo sapiens

<400> SEQUENCE: 3

Met Thr Ser Ser Leu Leu Ala Phe Leu Leu Ala Pro Thr Thr
1               5                   10                  15

Val Ala Thr Pro Arg Ala Gly Gly Gln Cys Pro Ala Cys Gly Gly Pro
            20                  25                  30

Thr Leu Glu Leu Glu Ser Gln Arg Glu Leu Leu Asp Leu Ala Lys
            35                  40                  45

Arg Ser Ile Leu Asp Lys Leu His Leu Thr Gln Arg Pro Thr Leu Asn
            50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
                    85                  90                  95

Glu Ile Ile Ser Phe Ala Glu Thr Gly Leu Ser Thr Ile Asn Gln Thr
                100                 105                 110

Arg Leu Asp Phe His Phe Ser Ser Asp Arg Thr Ala Gly Asp Arg Glu
                115                 120                 125

Val Gln Gln Ala Ser Leu Met Phe Phe Val Gln Leu Pro Ser Asn Thr
            130                 135                 140

Thr Trp Thr Leu Lys Val Arg Val Leu Val Leu Gly Pro His Asn Thr
145                 150                 155                 160

Asn Leu Thr Leu Ala Thr Gln Tyr Leu Leu Glu Val Asp Ala Ser Gly
                165                 170                 175

Trp His Gln Leu Pro Leu Gly Pro Glu Ala Gln Ala Ala Cys Ser Gln
            180                 185                 190

Gly His Leu Thr Leu Glu Leu Val Leu Glu Gly Gln Val Ala Gln Ser
                195                 200                 205

Ser Val Ile Leu Gly Gly Ala Ala His Arg Pro Phe Val Ala Ala Arg
            210                 215                 220

Val Arg Val Gly Gly Lys His Gln Ile His Arg Arg Gly Ile Asp Cys
225                 230                 235                 240

Gln Gly Gly Ser Arg Met Cys Cys Arg Gln Glu Phe Val Asp Phe
                245                 250                 255

Arg Glu Ile Gly Trp His Asp Trp Ile Ile Gln Pro Glu Gly Tyr Ala
                260                 265                 270

Met Asn Phe Cys Ile Gly Gln Cys Pro Leu His Ile Ala Gly Met Pro
            275                 280                 285

Gly Ile Ala Ala Ser Phe His Thr Ala Val Leu Asn Leu Leu Lys Ala
        290                 295                 300

Asn Thr Ala Ala Gly Thr Thr Gly Gly Gly Ser Cys Cys Val Pro Thr
305                 310                 315                 320

Ala Arg Arg Pro Leu Ser Leu Leu Tyr Tyr Asp Arg Asp Ser Asn Ile
                325                 330                 335

Val Lys Thr Asp Ile Pro Asp Met Val Val Glu Ala Cys Gly Cys Ser
                340                 345                 350

<210> SEQ ID NO 4
<211> LENGTH: 352
<212> TYPE: PRT
<213> ORGANISM: Mouse
```

```
<400> SEQUENCE: 4

Met Ala Ser Ser Leu Leu Ala Leu Leu Phe Leu Thr Pro Thr Thr
1               5                   10                  15

Val Val Asn Pro Lys Thr Glu Gly Pro Cys Pro Ala Cys Trp Gly Ala
            20                  25                  30

Ile Phe Asp Leu Glu Ser Gln Arg Glu Leu Leu Asp Leu Ala Lys
            35                  40                  45

Lys Ser Ile Leu Asp Lys Leu His Leu Ser Gln Arg Pro Ile Leu Ser
    50                  55                  60

Arg Pro Val Ser Arg Gly Ala Leu Lys Thr Ala Leu Gln Arg Leu Arg
65                  70                  75                  80

Gly Pro Arg Arg Glu Thr Leu Leu Glu His Asp Gln Arg Gln Glu Glu
                85                  90                  95

Tyr Glu Ile Ile Ser Phe Ala Asp Thr Asp Leu Ser Ser Ile Asn Gln
                100                 105                 110

Thr Arg Leu Glu Phe His Phe Ser Gly Arg Met Ala Ser Gly Met Glu
            115                 120                 125

Val Arg Gln Thr Arg Phe Met Phe Val Gln Phe Pro His Asn Ala
    130                 135                 140

Thr Gln Thr Met Asn Ile Arg Val Leu Val Leu Arg Pro Tyr Asp Thr
145                 150                 155                 160

Asn Leu Thr Leu Thr Ser Gln Tyr Val Val Gln Val Asn Ala Ser Gly
                165                 170                 175

Trp Tyr Gln Leu Leu Leu Gly Pro Glu Ala Gln Ala Ala Cys Ser Gln
                180                 185                 190

Gly His Leu Thr Leu Glu Leu Val Pro Glu Ser Gln Val Ala His Ser
            195                 200                 205

Ser Leu Ile Leu Gly Trp Phe Ser His Arg Pro Phe Val Ala Ala Gln
    210                 215                 220

Val Arg Val Glu Gly Lys His Arg Val Arg Arg Gly Ile Asp Cys
225                 230                 235                 240

Gln Gly Gly Ser Arg Met Cys Cys Arg Gln Glu Phe Phe Val Asp Phe
                245                 250                 255

Arg Glu Ile Gly Trp Asn Asp Trp Ile Ile Gln Pro Glu Gly Tyr Ala
                260                 265                 270

Met Asn Phe Cys Thr Gly Gln Cys Pro Leu His Val Ala Gly Met Pro
    275                 280                 285

Gly Ile Ser Ala Ser Phe His Thr Ala Val Leu Asn Leu Leu Lys Ala
            290                 295                 300

Asn Ala Ala Ala Gly Thr Thr Gly Arg Gly Ser Cys Cys Val Pro Thr
305                 310                 315                 320

Ser Arg Arg Pro Leu Ser Leu Leu Tyr Tyr Asp Arg Asp Ser Asn Ile
                325                 330                 335

Val Lys Thr Asp Ile Pro Asp Met Val Val Glu Ala Cys Gly Cys Ser
            340                 345                 350

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: primer
```

-continued

```
<400> SEQUENCE: 5

Met His His His His His His Lys Leu Ile
1               5                   10

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 6
caacagcagc gtgaagttgg ag                                          22

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
actaatgtca aacacgtacc tctg                                        24
```